(12) United States Patent
Ishikawa

(10) Patent No.: US 10,796,794 B2
(45) Date of Patent: Oct. 6, 2020

(54) DELETION OF MEDICAL IMAGES IN CLOUD-BASED STORAGE

(71) Applicant: Konica Minolta Healthcare Americas, Inc., Wayne, NJ (US)

(72) Inventor: Takayuki Ishikawa, Wayne, NJ (US)

(73) Assignee: Konica Minolta Healthcare Americas, Inc., Wayne, NJ (US)

( * ) Notice: Subject to any disclaimer, the term of this patent is extended or adjusted under 35 U.S.C. 154(b) by 58 days.

(21) Appl. No.: 15/938,971

(22) Filed: Mar. 28, 2018

(65) Prior Publication Data

US 2019/0304589 A1 Oct. 3, 2019

(51) Int. Cl.
*G16H 30/20* (2018.01)
*H04L 29/08* (2006.01)

(52) U.S. Cl.
CPC .............. *G16H 30/20* (2018.01); *H04L 67/06* (2013.01); *H04L 67/1097* (2013.01)

(58) Field of Classification Search
None
See application file for complete search history.

(56) References Cited

U.S. PATENT DOCUMENTS

| | | | | |
|---|---|---|---|---|
| 2006/0083442 A1* | 4/2006 | Loukipoudis | .......... | G16H 30/20 382/305 |
| 2008/0212855 A1* | 9/2008 | Shibuya | ................ | G06F 19/321 382/128 |
| 2011/0110568 A1* | 5/2011 | Vesper | .................. | G06F 19/321 382/128 |
| 2011/0320469 A1* | 12/2011 | Canessa | ................. | G16H 50/30 707/758 |
| 2014/0279854 A1* | 9/2014 | Scanlon | ................ | G06F 16/162 707/609 |
| 2017/0091464 A1* | 3/2017 | Richards | ............... | H04L 63/102 |
| 2017/0235880 A1* | 8/2017 | Wright | ................ | G06F 21/6245 705/2 |

* cited by examiner

*Primary Examiner* — Clayton R Williams
*Assistant Examiner* — Christopher B Robinson
(74) *Attorney, Agent, or Firm* — Osha Liang LLP

(57) ABSTRACT

A method is provided for controlling automatic deletion of medical images in a universal viewer system that shares the medical images between a cloud server and a plurality of healthcare facilities connected to the cloud server. The method is executed by the cloud server and includes: receiving, from a user at one of the healthcare facilities, an automatic deletion request that comprises a target deletion period and a deletion start time; determining, after the deletion start time has elapsed, a target medical image based on the target deletion period; retrieving an access history of the target medical image; terminating, in response to determining based on the access history that the target medical image is accessed by a plurality of users, the automatic deletion request without deleting the target medical image; storing in a memory a result of the automatic deletion request; and causing the result of the deletion request to be displayed on a display of at least one of the healthcare facilities.

21 Claims, 15 Drawing Sheets

Periodic Image Deletion Settings

Deletion Based On: ● Image Receipt Date  ○ Diagnosis Date

Data Type ☑ Image Data

Setting Period ▶ Year  ▢ Date

Delete all data prior to the setting period

Deletion Start Time 0 : 00

Exceptions ☑ Image data accessed by multiple users (Radiologists)

FIG. 7

DELETION OF MEDICAL IMAGES IN CLOUD-BASED STORAGE

BACKGROUND

Medical images and medical data play a crucial role in the diagnosis of a patient. Healthcare facilities (e.g., hospitals) have realized the benefits of electronically storing medical images and medical data. The digitalization of the medical images and data ("medical data") not only enables healthcare professionals to easily access medical images and medical data, but also enables the images and data to be easily shared between multiple healthcare facilities through the use of physical mediums such as compact discs (CDs), digital video discs (DVDs), and Universal Serial Bus (USB) flash drives.

More recently, cloud-based storage systems have emerged as a way to improve efficiency and accessibility of information. In general, a "cloud" can be understood as an online storage system that provides remote, on-demand access of computing resources and data over the Internet to multiple computers and devices in various locations. Cloud-based storage may be provided by vendors who use remote or off-site data centers in various locations for storage of data such as medical images. The vendors of the cloud-based storage may also provide a common viewing system ("a universal viewer") that allows the healthcare facilities to retrieve a complete set of the patient's medical data taken or stored at other healthcare facilities through a single request.

SUMMARY

In general, in one aspect, the invention relates to a method for controlling automatic deletion of medical images in a universal viewer system that shares the medical images between a cloud server and a plurality of healthcare facilities connected to the cloud server. The method comprising: receiving, by the cloud server and from a user at one of the healthcare facilities, an automatic deletion request that comprises a target deletion period and a deletion start time; determining, by the cloud server and after the deletion start time has elapsed, a target medical image based on the target deletion period; retrieving, by the cloud server, an access history of the target medical image; terminating, by the cloud server in response to determining based on the access history that the target medical image is accessed by a plurality of users, the automatic deletion request without deleting the target medical image; storing in a memory, by the cloud server, a result of the automatic deletion request; and causing, by the cloud server, the result of the deletion request to be displayed on a display of at least one of the healthcare facilities.

In general, in one aspect, the invention relates to a non-transitory computer-readable medium (CRM) storing instructions that causes a cloud server to perform an operation for controlling automatic deletion of medical images in a universal viewer system that shares the medical images between the cloud server and a plurality of healthcare facilities connected to the cloud server. The operation comprising causing the cloud server to: receive, from a user at one of the healthcare facilities, an automatic deletion request that comprises a target deletion period and a deletion start time; determine, after the deletion start time has elapsed, a target medical image based on the target deletion period; retrieve an access history of the target medical image; terminate, in response to determining based on the access history that the target medical image is accessed by a plurality of users, the automatic deletion request without deleting the target medical image; store, in a memory, a result of the automatic deletion request; and cause the result of the deletion request to be displayed on a display of at least one of the healthcare facilities.

In general, in one aspect, the invention relates to a universal viewer system that controls deletion of medical images. The universal viewer system comprising: a cloud server; and a plurality of local computers disposed at healthcare facilities connected to the cloud server, wherein the universal viewer system shares the medical images between the cloud server and the local computers. The cloud server: receives, from a user at one of the healthcare facilities, an automatic deletion request that comprises a target deletion period and a deletion start time; determines, after the deletion start time has elapsed, a target medical image based on the target deletion period; retrieves an access history of the target medical image; terminates, in response to determining based on the access history that the target medical image is accessed by a plurality of users, the automatic deletion request without deleting the target medical image; stores, in a memory, a result of the automatic deletion request; and causes the result of the deletion request to be displayed on a display of at least one of the healthcare facilities.

Other aspects and advantages of the invention will be apparent from the following description and the appended claims.

BRIEF DESCRIPTION OF DRAWINGS

FIG. 7 shows an implementation example in accordance with one or more embodiments.

DETAILED DESCRIPTION

Figure 1A:
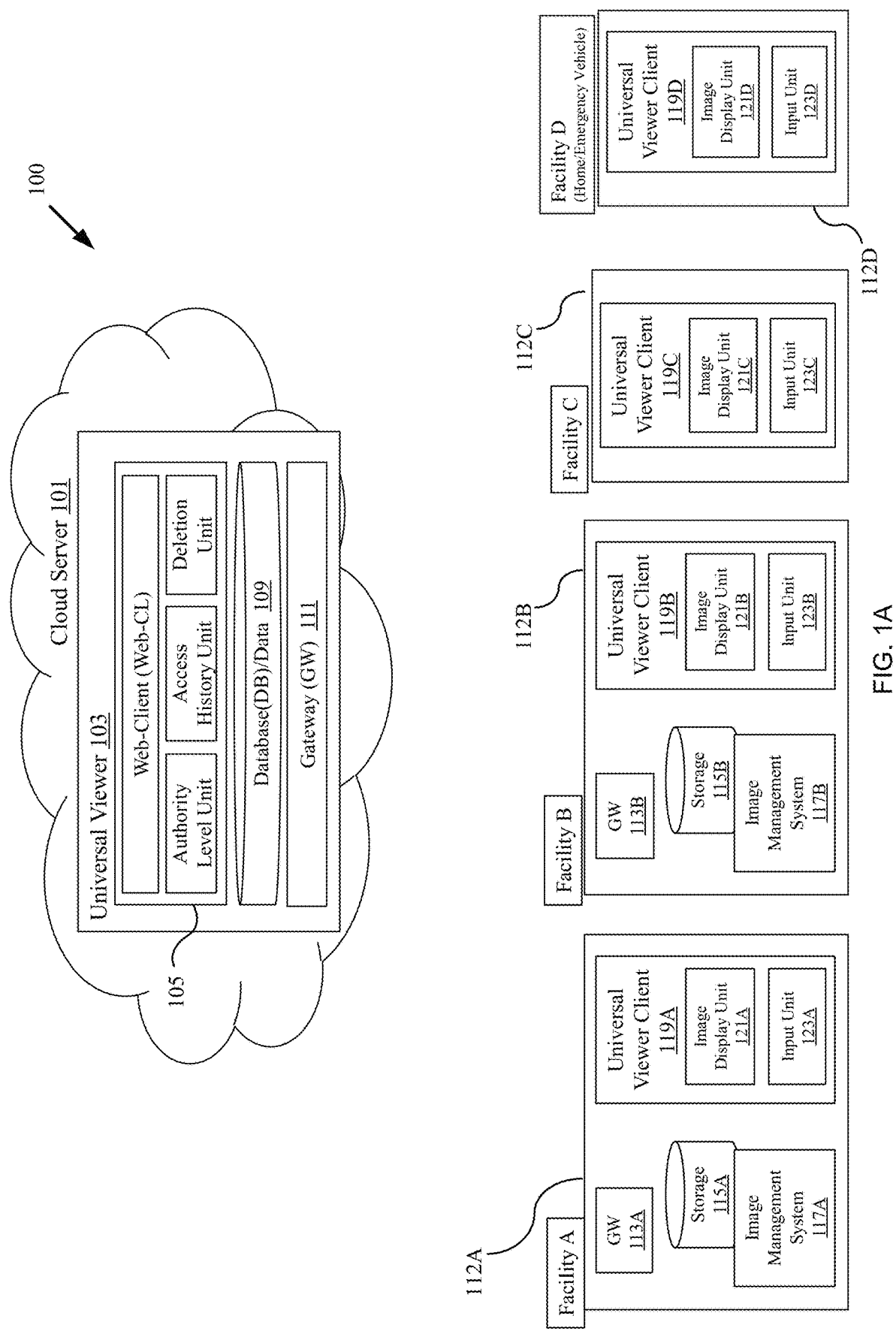
FIGS. 1A-1B show a system in accordance with one or more embodiments of the invention.

Specific embodiments will now be described in detail with reference to the accompanying figures. Like elements in the various figures are denoted by like reference numerals for consistency. Like elements may not be labeled in all figures for the sake of simplicity.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers does not imply or create a particular ordering of the elements or limit any element to being only a single element unless expressly disclosed, such as by the use of the terms "before," "after," "single," and other such terminology. Rather, the use of ordinal numbers is to distinguish between the elements. By way of an example, a first element is distinct from a second element, and the first element may encompass more than one element and succeed (or precede) the second element in an ordering of elements.

It is to be understood that the singular forms "a," "an," and "the" include plural referents unless the context clearly dictates otherwise. Thus, for example, reference to "a horizontal beam" includes reference to one or more of such beams.

Terms such as "approximately," "substantially," etc., mean that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Although multiple dependent claims are not introduced, it would be apparent to one of ordinary skill that the subject matter of the dependent claims of one or more embodiments may be combined with other dependent claims.

In general, one or more embodiments of the invention provide a method, a non-transitory computer readable medium, and a system configured for deleting medical data (i.e., a patient's complete medical records including all medical images, reports, files, etc.) shared between healthcare facilities.

With a universal viewer in accordance with one or more embodiments, healthcare facilities that work together as part of a group or network are able to coordinate and deliver a broad spectrum of services to patients of those healthcare facilities. For example, the network may comprise healthcare facilities that are part of the same hospital group or healthcare facilities within a particular region (e.g., a regional medical network). According to one or more embodiments, healthcare facilities that are part of the network ("in-network healthcare facility") can more effectively utilize the universal viewer to share medical data for patients who frequent one or more of the in-network healthcare facilities.

According to one or more embodiments, each of the in-network healthcare facilities may be associated with one of a cloud-based storage system, a Picture Archiving and Communication System (PACS), or a cloud-based PACS provided by the same vendor or a different vendor. Specifically, each of the in-network healthcare facilities may utilize a different system for storing medical data and may also utilize a unique network for inter-facility communication. For example, each in-network healthcare facility may have a unique security protocol, data encryption method, and network safety and access protocol.

According to one or more embodiments, a patient's medical images and data (herein referred to as "medical images") may be stored in a Digital Imaging and Communications in Medicine (DICOM) format image. The patient's medical images may also include multiple (e.g., tens to several hundreds of) DICOM format images. The DICOM format image may include metadata that stores patient information and/or medical diagnosis related data such as patient ID, patient name, patient date of birth (DOB), patient gender, study date of the diagnosis, accession number of the medical image, and the modality used to perform the diagnosis.

In one or more embodiments, a deletion of a medical image may be the deletion of all data associated with the medical image. Alternatively, the deletion of the medical image may be the deletion of only part of the data of the medical image (e.g., one or more of the tens to several hundreds of the DICOM images).

According to one or more embodiments, in the event that a patient's medical data is updated (e.g., deleted) at any one of the multiple in-network healthcare facilities, the universal viewer displays a message to notify all other in-network healthcare facilities that have previously retrieved the medical data. This enables all of the users among the in-network healthcare facilities to be provided with the most recent and up-to-date medical data.

Figure 1B:
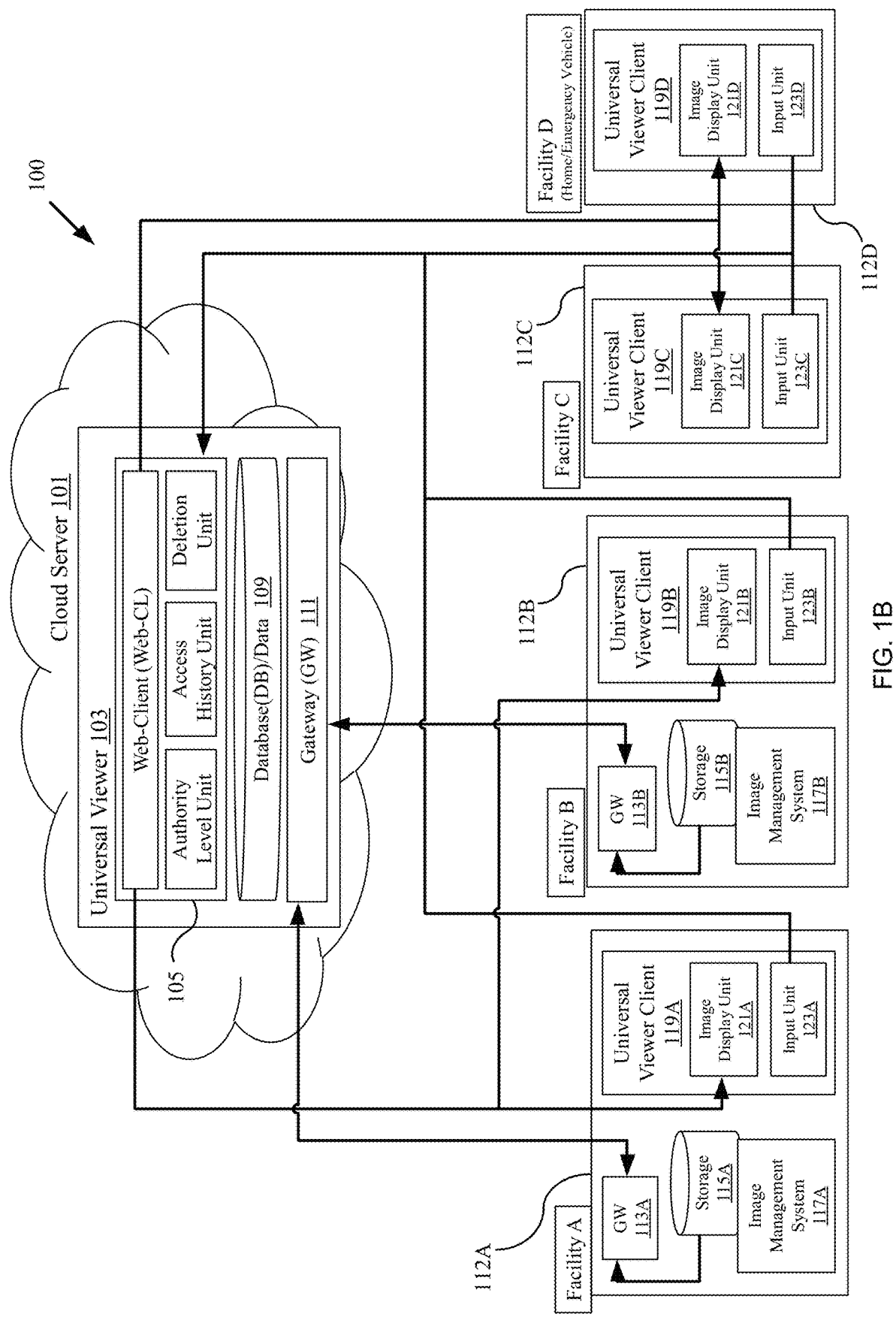

FIGS. 1A and 1B show a system (100) in accordance with one or more embodiments of the invention. As shown, the system (100) includes a cloud server (101) and multiple healthcare facilities (Facility A-D). The cloud server (100) includes a universal viewer computing device (103) that is installed with the universal viewer application. The universal viewer computing device (103) includes a processor (105), a database (DB) (109) and a cloud gateway (GW) device (111). The universal viewer computing device (103) may be an industrial-use computer that includes one or more computer processor(s), associated memory (e.g., random access memory (RAM), cache memory, flash memory, etc.), one or more storage device(s) (e.g., a hard disk, an optical drive such as a compact disk (CD) drive or digital versatile disk (DVD) drive, a flash memory stick, etc.), and numerous other elements and functionalities. The universal viewer computing device (103) may be managed by the vendor(s) that provide the services of the cloud-based PACS.

In one or more embodiments of the invention, the processor (105) may be configured with a Web-Client (web-CL) application for the universal viewer computing device (103) that allows each healthcare facility (Facilities A-D) to access the universal viewer application via a web-browser. For example, the universal viewer application may be accessed as a web page by inputting a uniform resource locator (URL) (e.g., a web address) associated with the web-CL into the search bar of the web-browser.

In one or more embodiments, the processor (105) may further be configured to include an authority level unit that determines an authority level of a user (e.g., personnel at the healthcare facilities) accessing the web-CL, an access history unit that manages an access history of all medical images stored in the DB (109), and a deletion unit that performs deletion of the medical images. The web-CL, authority level unit, access history unit, and deletion unit may be applications and programs configured to be executed by the processor. The functions of the authority level unit, the access history unit, and the deletion unit are described in more detail below with reference to FIGS. 2A-2C, 3A-3B, and 4A-4B.

In one or more embodiments of the invention, the DB (109) may be configured as a remote medical repository that stores medical images remotely on the cloud server (101). For example, the remote medical repository may be a virtual data room (VDR) or a database (or group of databases) accessed remotely via the Internet. In one or more embodiments, the DB (109) may also store authority level information of users at the healthcare facilities and access history of each medical image stored in the DB (109). The access history of each medical image may be stored as metadata in the corresponding medical image.

In one or more embodiments of the invention, the cloud GW device (111) may be a hub or a local area network (LAN) at the facility where the cloud server (101) is physically disposed. The cloud GW device (111) may be configured as a relay point between the cloud server (101) and the healthcare facilities (Facility A-D) that enables each healthcare facility (Facilities A-D) to communicate and share (i.e., retrieve and transmit) medical images with the cloud server (101).

In one or more embodiments of the invention, the system (100) further includes local computing devices (112A-112D) (i.e., local computers) that are disposed in the healthcare facilities (Facility A-D). Each healthcare facility (Facility A-D) may be any type of facility that provides medical care such as a public hospital, a private hospital, a medical clinic, a dental clinic, an emergency vehicle (e.g., ambulance), a mobile clinic vehicle, etc. Each local computing device (112A-112D) may correspond to a personal computer (PC), a laptop, a mobile computing device (e.g., tablet PC, smartphone, etc.), a server, a mainframe, a kiosk, etc. In one or more embodiments, the local computing devices (112A-112D) at each in-network healthcare facility may be configured as a local medical server.

In one or more embodiments of the invention, depending on the type of healthcare facility, the local computing devices (112A-112D) may include a local GW device (113A-113B), a central storage (115A-115B), an image management system (117A-117B), a universal viewer client application (119A-119B), an image display unit (121A-121D), and an input unit (123A-123D). For example, assume that Facilities A and B are public or private hospitals with larger facility space. The local computing devices (112A-112B) of Facilities A and B may include the central storage (115A-115B) and the image management system (117B) that manages and stores (i.e., backs-up) large amounts of data locally at the facilities, and the gateway device (113) to synchronize the locally-managed and stored data with the cloud server (101). As another example, assume that Facilities C and D are smaller facilities such as medical clinics, dental clinics, mobile clinics, and ambulances that do not have the capacity to store and manage (i.e., back-up) large amounts of data locally. The computing devices (112C-112D) of Facilities C and D may only include the minimum required systems such as the universal viewer client application (119C-119D), the image display unit (121C-121D), and the input unit (123C-123D) to be able to share (i.e., retrieve and transmit) data with the universal viewer computing device (103).

In one or more embodiments of the invention, the combination of the local gateway device (113A-113B), the central storage (115A-115B), and the image management system (117A-117B) enables healthcare facilities A and B to synchronize data with the cloud server (101) in order to manage and store (i.e., back-up) large amounts of data that are stored on the cloud server (101) locally at the facilities. The central storage (115A-115B) may be composed of a cluster of servers disposed in a local server room of Facilities A and B. The image management system (117A-117B) may be an independent application stored in the local computing devices (112A-112B) that allows the users at Facilities A and B to compile and process the medical images taken locally at the facilities without using the functions of the universal viewer client application (119A-119B). The image management system (117A-117B) may be operated and provided by the same or a different vendor(s) from the vendor(s) that provides the services of the cloud-based PACS.

In one or more embodiments of the invention, the universal viewer client application (119A-119D) may be stored on all of the local computing devices (112A-112B) and may be downloaded to the local computing devices (112A-112B) as a plug-in of a web-browser application with a graphical user interface ("GUI") that allows the users to access the universal viewer application stored on the cloud server (101). Alternatively, the universal viewer client application (119A-119D) may be accessed as a web page by inputting a uniform resource locator (URL) (e.g., a web address) associated with the web-CL application stored on the cloud server (101) into the search bar of the web-browser.

In one or more embodiments of the invention, the universal viewer client application (119A-119D) includes the image display unit (121A-121D) that causes a display (e.g., a monitor, a screen, etc.) of the local computing devices (112A-112D) to display all of the contents associated with the universal viewer client application (119A-119D) (e.g., the GUI, the medical images, etc.). In one or more embodiments, the universal viewer client application (119A-119D) also includes the input unit (123A-123D) that receives user input commands through built in and/or peripheral input devices (e.g., a mouse, a keyboard, a touchscreen, etc.) of the local computing devices (112A-112D). In one or more embodiments, the image display unit (121A-121D) and the input units (123A-123D) may be sub-applications (i.e., sub-functions) of the universal viewer client application (119A-119D).

In one or more embodiments of the invention, as seen in FIG. 1B, the image management system (117A-117B) of Facilities A and B share (i.e., retrieve and transmit) medical images with the cloud server (101) through bilateral communication between the local GW devices (113A-113B) and the cloud GW device (111).

In one or more embodiments, each of the healthcare facilities (Facility A-D) may be on a different internet network ("network"), which in turn may be different from the network of the cloud server (101). Therefore, the healthcare facilities (Facility A-D) may communicate with the cloud server (101) through the local gateway device (113A-113B), a separate device that connects and passes data between two different devices connected on different networks (e.g., a router, a modem, etc.), and/or directly through a mobile communication network (e.g., 3G and LTE communication networks).

In one or more embodiments of the invention, as seen in FIG. 1B, the processor (105) may receive requests (e.g., medical images retrieval, storage, synchronization, deletion, etc. requests) from users at the healthcare facilities (Facility A-D) through the respective input units (123A-123D). In one or more embodiments, the web-CL application on the cloud server (101) may transmit instructions to the image display unit (121A-121D) of the universal viewer client application (119A-119D) to cause the local computing devices (112A-112D) to display a result of the request (e.g., a retrieved medical image, a synchronization result, a storage result, a deletion result, etc.).

Figure 2A:
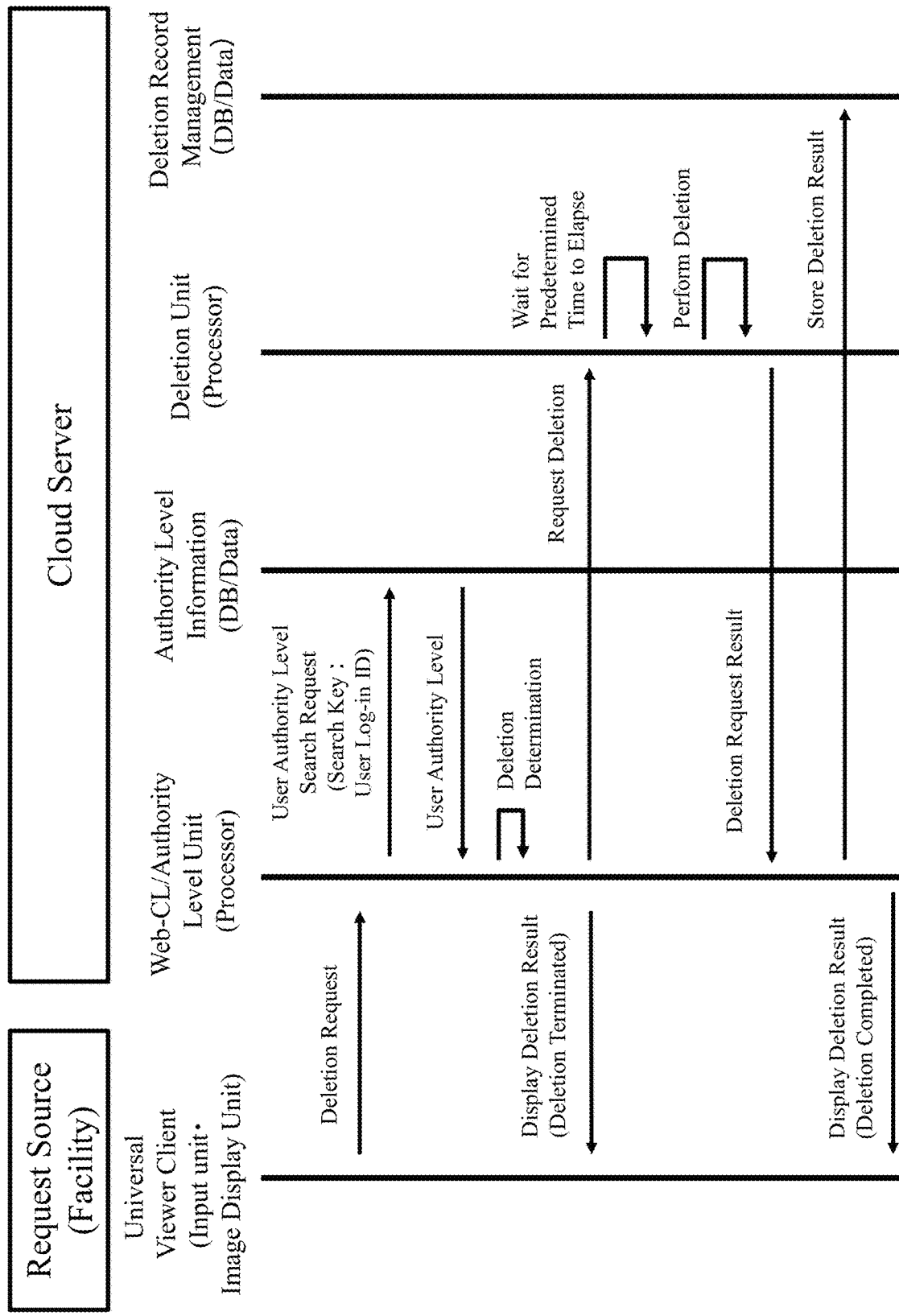
FIGS. 2A-2C show diagrams in accordance with one or more embodiments of the invention.
Figure 2B:
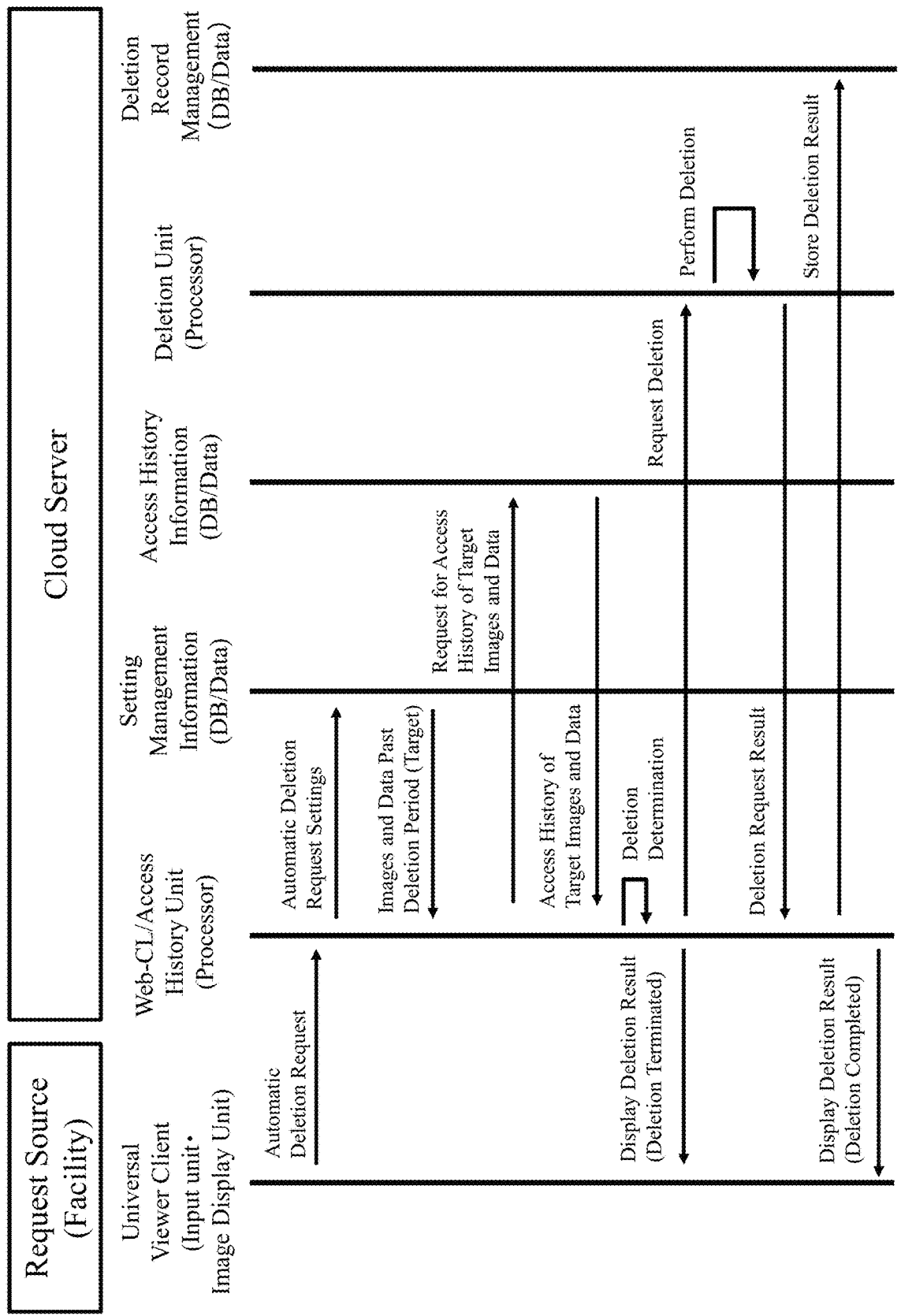

FIGS. 2A and 2B show communication diagrams in accordance with one or more embodiments of the invention. The communication diagram illustrates a communication method of one or more embodiments that may be implemented by the system as shown in FIGS. 1A and 1B. The communication diagram illustrates the path of the signals transmitted in response to a request from one of the healthcare facilities to delete medical images stored in the cloud server.

In one or more embodiments of the invention, FIG. 2A shows a communication diagram that illustrates a path of signals transmitted in response to a medical image deletion request (herein referred to as "deletion request") received from one of the healthcare facilities. In the description of FIG. 2A below, the actions performed by the processor are described based on execution of the functions associated with of the web-CL application, the authority level unit, and the deletion unit.

In one or more embodiments of the invention, the deletion request originates from a local computing device of one of the healthcare facilities (herein referred to as the "request source"). The deletion request includes user identification (user ID) of the user that initiated the deletion request and one or more information of the medical images (e.g., patient ID, patient name, patient date of birth (DOB), patient gender, study date of the diagnosis, accession number of the medical image, the modality used to perform the diagnosis, etc.) to be deleted.

In one or more embodiments, the deletion request is received by the processor of the cloud server. The processor transmits a user authority level search request to the DB to retrieve authority level information of the user that transmitted the deletion request. The user authority level search request includes the user ID.

In one or more embodiments of the invention, the DB retrieves the user authority level information associated with the user ID and transmits the user authority level information back to the processor. Upon receiving the user authority level information, the processor determines whether the authority level information matches or is higher than a pre-configured authority level (i.e., a specified authority level). The pre-configured authority level is a minimum level of authority required for any users at the healthcare facilities to delete medical images. The pre-configured authority level may be determined by the vendor of the cloud-based PACS and is applied universally to all deletion requests from all healthcare facilities. For example, assume that a user must at least be a physician (i.e., doctor) to delete medical images. The pre-configured authority level is set to "physician," and all users with authority levels under a physician (e.g., reception staff, nurses, etc.) are unable to delete medical images.

In one or more embodiments of the invention, if the authority level information retrieved by the processor is lower than the pre-configured authority level, the processor transmits a signal to the local computing device that causes the universal viewer client application to display that the deletion request was terminated or that the deletion request cannot be processed. In one or more embodiments, if the authority level information retrieved by the processor matches or is higher than the pre-configured specified authority level, the processor executes a deletion of the medical images specified in the deletion request.

In one or more embodiments of the invention, upon executing the deletion, the processor non-permanently deletes the medical images from a listing in the DB and waits for a predetermined time to elapse before permanently deleting all files associated with the medical images. In one or more embodiments, the predetermined time is based on the authority level of the user requesting the deletion. The predetermined time for users with lower authority levels may be longer than the predetermined time for users with higher authority levels. In one or more embodiments, the predetermined time for each authority level may be pre-configured by the vendor of the cloud-based PACS. The predetermined time may range between instant deletion to deletion after one or more days, months, or years. For example, assume that the user is a system administrator and that the system administrator has the highest level of authority. The predetermined time set for the system administrator may be very small or zero (i.e., instant deletion). As another example, assume that the user is a tertiary physician and that the tertiary physician has the lowest level of authority (i.e., the minimum authority level that matches the pre-configured authority level). The predetermined time set for the tertiary physician may range between a few days or months to one or more years.

In one or more embodiments of the invention, upon executing the permanent deletion of medical images, the processor transmits a signal to the local computing device that causes the universal viewer client application to display that the deletion request was successful. Additionally, the processor causes the DB to store a result of the deletion request. This is described in more detail below in reference to FIGS. 6A and 6B.

In one or more embodiments of the invention, users of any authority level may restore medical images that have not been permanently deleted. For example, prior to the lapse of the predetermined time, any user from any healthcare facility may transmit an undo-deletion request to the cloud server. Upon receipt of the undo-deletion request, the processor of the cloud server terminates the non-permanent deletion of the medical image. This is described in more detail below in reference to FIGS. 6A and 6B.

In one or more embodiments of the invention, FIG. 2B shows a communication diagram that illustrates a path of signals transmitted in response to an automatic medical image deletion request (herein referred to as "automatic deletion request") received from one of the healthcare facilities. In the description of FIG. 2B below, the actions performed by the processor are described based on execution of the functions associated with the web-CL application, the access history unit, and the deletion unit.

In one or more embodiments of the invention, the automatic deletion request originates from the request source. The automatic deletion request includes user identification (user ID) of the user that initiated the automatic deletion request, a target deletion period information, and a deletion start time information. The target deletion period information may include criteria for determining target medical images to be deleted such as a date criterion (e.g., image receipt date, study date, etc.), a data type to be deleted, and a time period for deletion set by the user. The study date may be the day that a user generates and/or examines the medical image. The deletion start time may be a count-down or a count-up timer, or a specific time of day (e.g., in 12-hour or 24-hour format) that specifies when the automatic deletion should be executed. In one or more embodiments, the target deletion period information and deletion start time information are set by the user through a GUI of the universal viewer client application. This is described in more detail below in reference to FIG. 7.

In one or more embodiments of the invention, the automatic deletion request is received by the processor of the cloud server. The processor transmits the target deletion period information to the DB and receives back all target medical images that match the criteria included in the target deletion period information. The processor transmits an access history request to the DB to retrieve access history for the target medical images and receives back the requested target history. In one or more embodiments, the access history may include information of all users that have previously accessed a medical image and timing information that indicates when target medical image was accessed (i.e., an access time).

In one or more embodiments of the invention, the processor determines, based on the received access history, whether the target medical images should be deleted. In one or more embodiments, target medical images with access histories that indicate multiple user access (by users of the same and/or different healthcare facilities) and/or recent access are not deleted. Alternatively, in one or more embodiments, if the medical image is accessed by only users of the same healthcare facility, the medical images may be deleted.

In one or more embodiments of the invention, target medical images with access histories that indicate only a single user access and no recent access by the single user are deleted. Target medical images with access histories that indicate only a single user access and recent access by the single user are not deleted. In one or more embodiments, the time frame that determines whether the target medical image or data was recently accessed may be pre-configured by the vendor(s) of the cloud-based PACS. Alternatively, the time frame may be set through the GUI of the universal viewer client while configuring the automatic deletion request.

In one or more embodiments of the invention, whether the target medical images should be deleted may also be based upon the authority level and/or job title of the user that previously accessed the target medical images. For example, target medical images that were previously accessed by a radiologist are not to be deleted. In one or more embodiments, the criteria for the authority level and/or type of user associated with medical images that are not to be deleted may be pre-configured by the vendor of the cloud-based PACS. Alternatively, the criteria may be set by the user through the GUI of the universal viewer client while configuring the automatic deletion request.

In one or more embodiments of the invention, based on whether the target medical images are deleted, the processor transmits a signal to the local computing device that causes the universal viewer client application to display that the deletion request was successful or terminated (i.e., the deletion request cannot be processed). In both situations, the processor also causes the DB to store a result of the automatic deletion request.

Figure 2C:
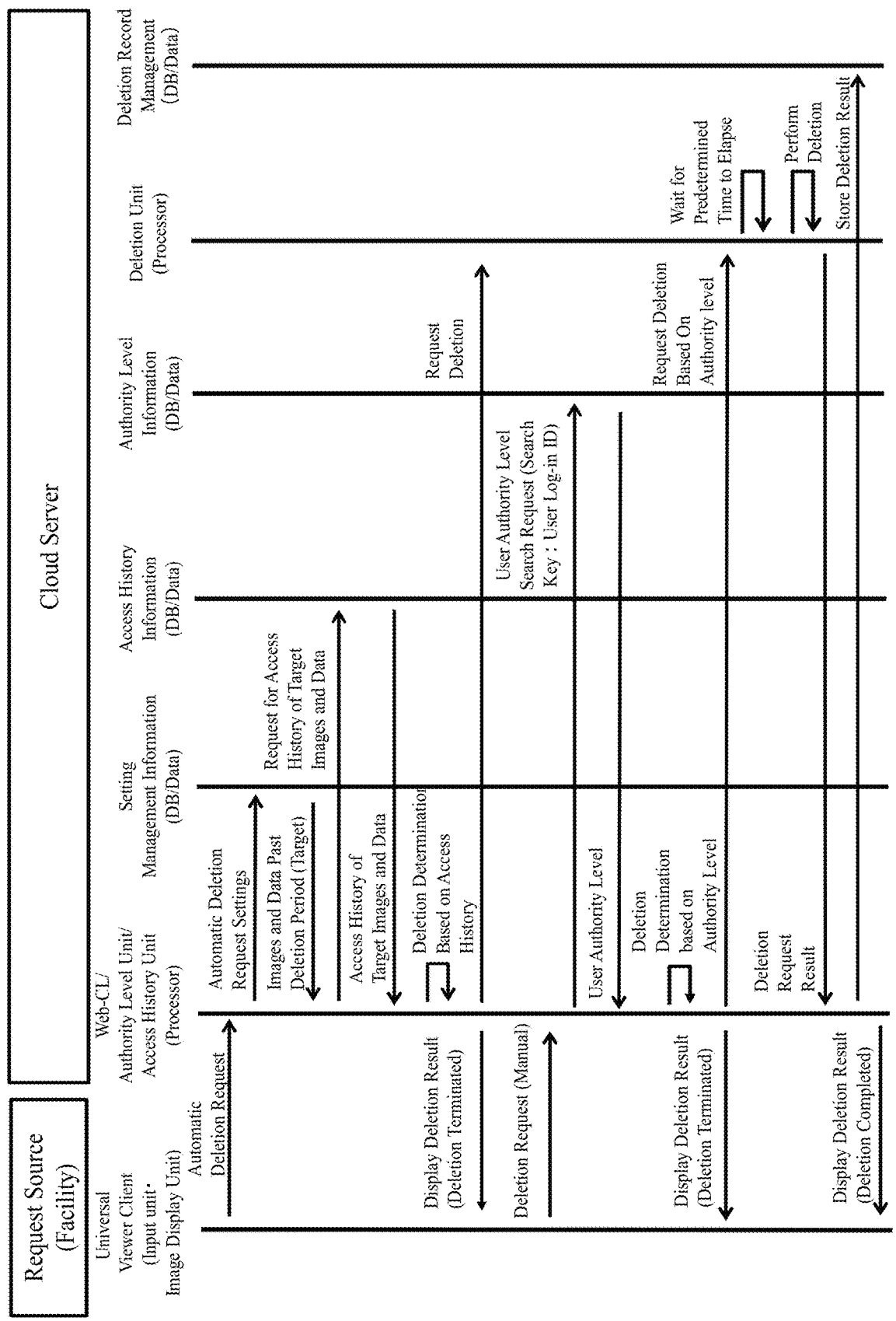

In accordance with one or more embodiments of the invention, FIG. 2C shows a communication diagram that illustrates a path of signals transmitted in response to transmission of both of the deletion request (i.e., the manual deletion request based on authority level) and the automatic deletion request, as described above in reference to FIGS. 2A and 2B, from one or more of the healthcare facilities. In the description of FIG. 2C below, the actions performed by the processor are described based on execution of the functions associated with the web-CL application, the authority level unit, the access history unit, and the deletion unit.

As seen in FIG. 2C, the deletion request (i.e., the manual deletion request based on authority level) may be received and executed by the cloud server while the cloud server is executing a previously received automatic deletion request. In other words, the cloud server may process the two requests in parallel. In one or more embodiments, the two requests may be received in any sequence and even at the same time. Furthermore, multiple manual deletion requests and automatic deletion requests may be received and executed by the cloud server in succession and/or at the same time.

Figure 3A:
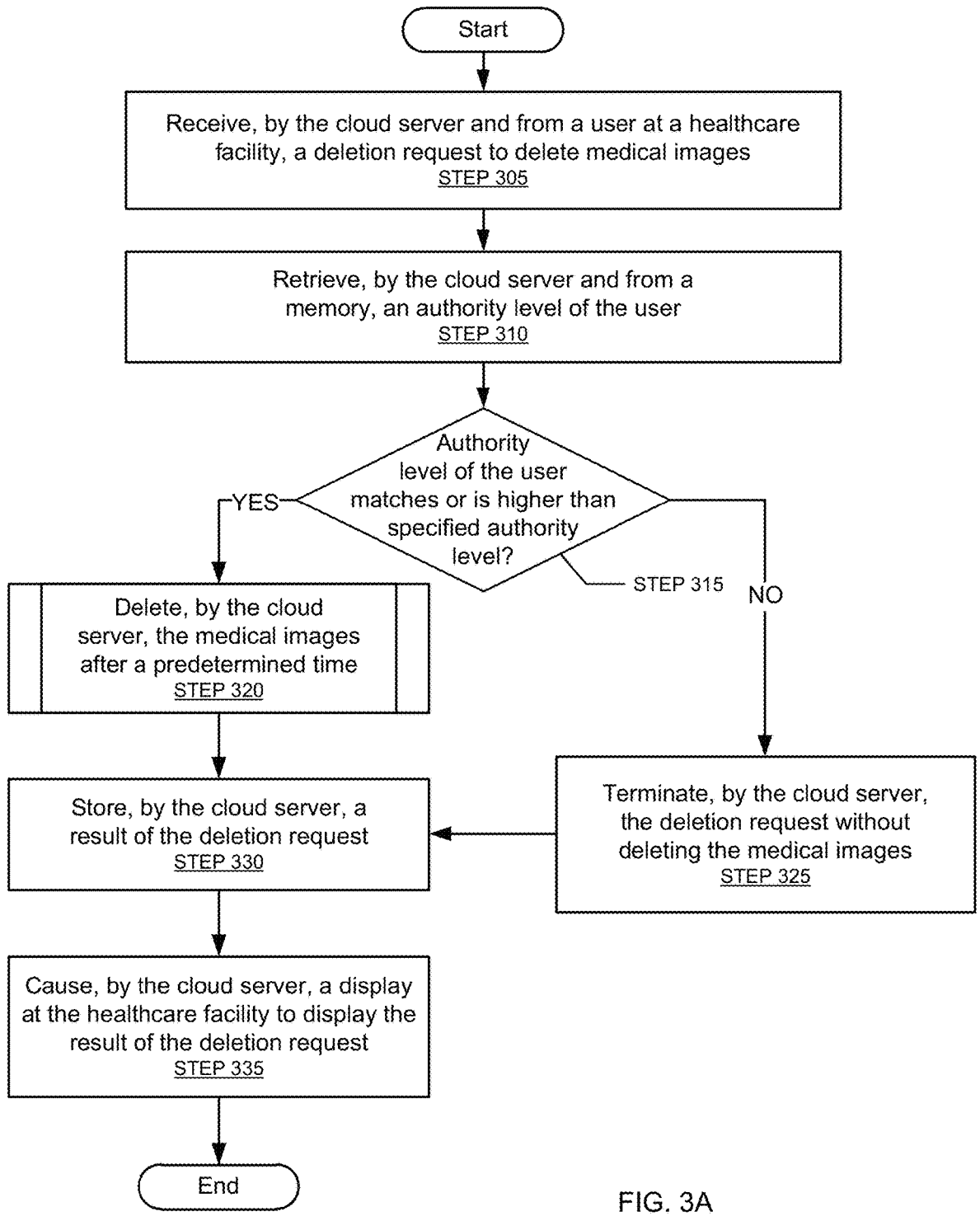
FIG. 3A shows a main flowchart in accordance with one or more embodiments of the invention.
Figure 3B:
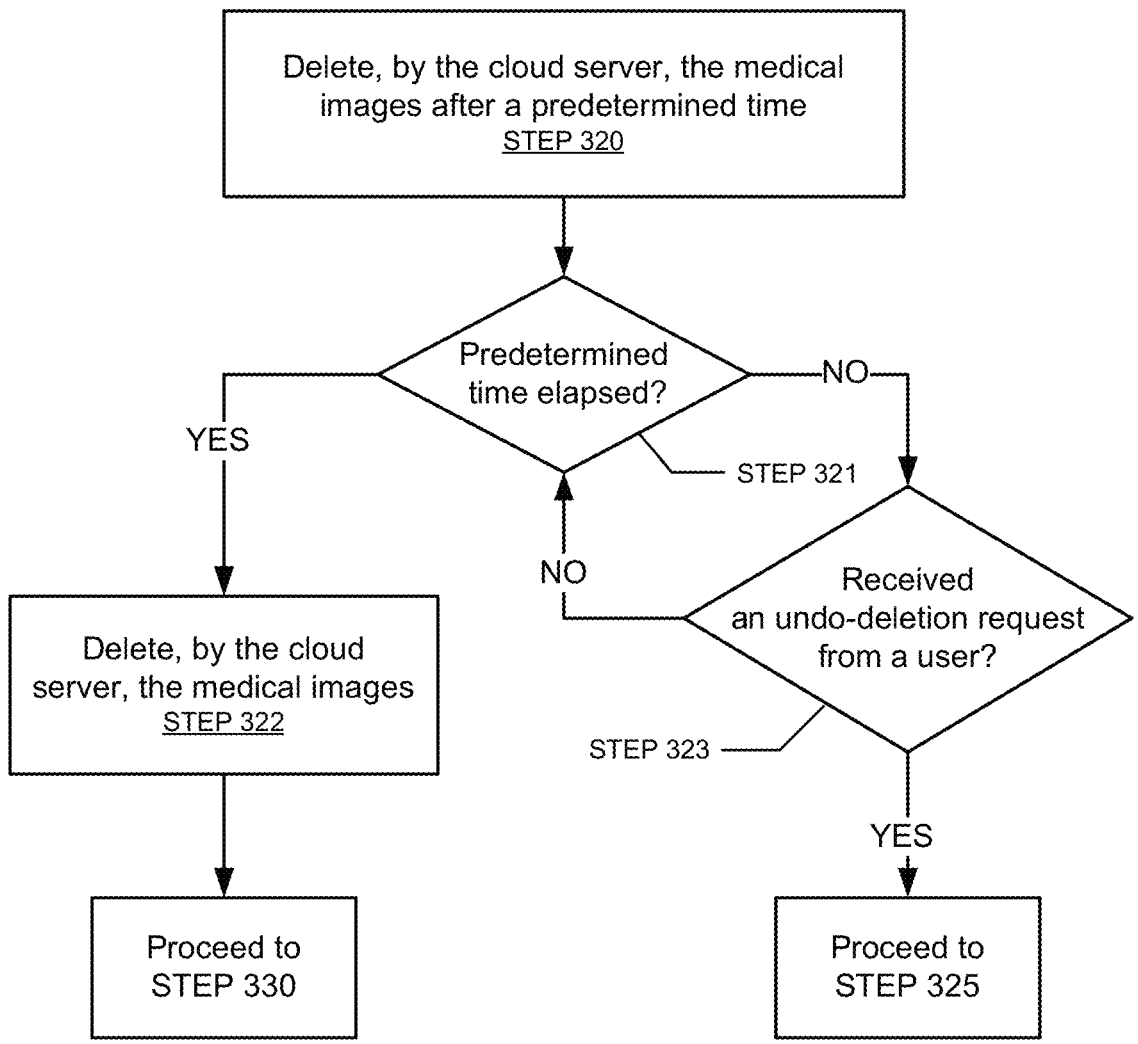
FIG. 3B shows a sub-flowchart in accordance with one or more embodiments of the invention.

FIGS. 3A and 3B show flowcharts in accordance with one or more embodiments of the invention. The flowcharts depict a process for deleting medical images in the cloud server based on user authority level. One or more of the steps in FIGS. 3A and 3B may be performed by the components of the system (100), discussed above in reference to FIGS. 1A-1B and 2A. In one or more embodiments of the invention, one or more of the steps shown in FIGS. 3A and 3B may be omitted, repeated, and/or performed in a different order than the order shown in FIGS. 3A and 3B. Accordingly, the scope of the invention should not be considered limited to the specific arrangement of steps shown in FIGS. 3A and 3B.

Referring to FIG. 3A, initially, in STEP 305, as discussed above in reference to FIGS. 1A-1B and 2A, the cloud server receives a deletion request from a user at one of the healthcare facilities connected to the cloud server.

In STEP 310, as discussed above in reference to FIGS. 1A-1B and 2A, the cloud server retrieves, from an internal database (DB) (i.e., a memory), an authority level information of the user that transmitted the deletion request.

In STEP 315, as discussed above in reference to FIGS. 1A-1B and 2A, the cloud server determines whether the authority level information of the user matches or is higher than a pre-configured authority level (i.e., a specified authority level).

In STEP 320, as discussed above in reference to FIGS. 1A-1B and 2A, the cloud server deletes the medical images associated with the deletion request after a predetermined time has elapsed if the authority level information of the user matches or is higher than a pre-configured authority level (i.e., a specified authority level).

In STEP 325, as discussed above in reference to FIGS. 1A-1B and 2A, the cloud server terminates the deletion request without deleting the medical images if the authority level information of the user is lower than the pre-configured authority level.

In STEP 330, as discussed above in reference to FIGS. 1A-1B and 2A, the cloud server stores the result of the deletion request in the DB.

In STEP 335, as discussed above in reference to FIGS. 1A-1B and 2A, the cloud server causes a local computing device at the healthcare facility where the deletion request originated to display the result of the deletion request.

FIG. 3B shows a sub-flowchart in accordance with one or more embodiments further expanding upon STEP 320 of the flow chart of FIG. 3A.

In STEP 321, as discussed above in reference to FIGS. 1A-1B and 2A, the cloud server determines whether the predetermined time has elapsed.

In STEP 322, as discussed above in reference to FIGS. 1A-1B and 2A, the cloud server deletes medical images associated with the deletion request. In one or more embodiments, the deletion in STEP 322 is a permanent deletion of all files associated with the to-be deleted medical images.

In STEP 323, as discussed above in reference to FIGS. 1A-1B and 2A, before the predetermined time has elapsed, the cloud server determines whether an undo-deletion request has been received from any user at any of the healthcare facilities. If an undo-deletion was not received, the process reverts to STEP 321 where the cloud server continues to determine whether the predetermined time has elapsed. If an undo-deletion was received, the process proceeds to STEP 325 where the cloud server terminates the deletion request without deleting the medical images.

Figure 4A:
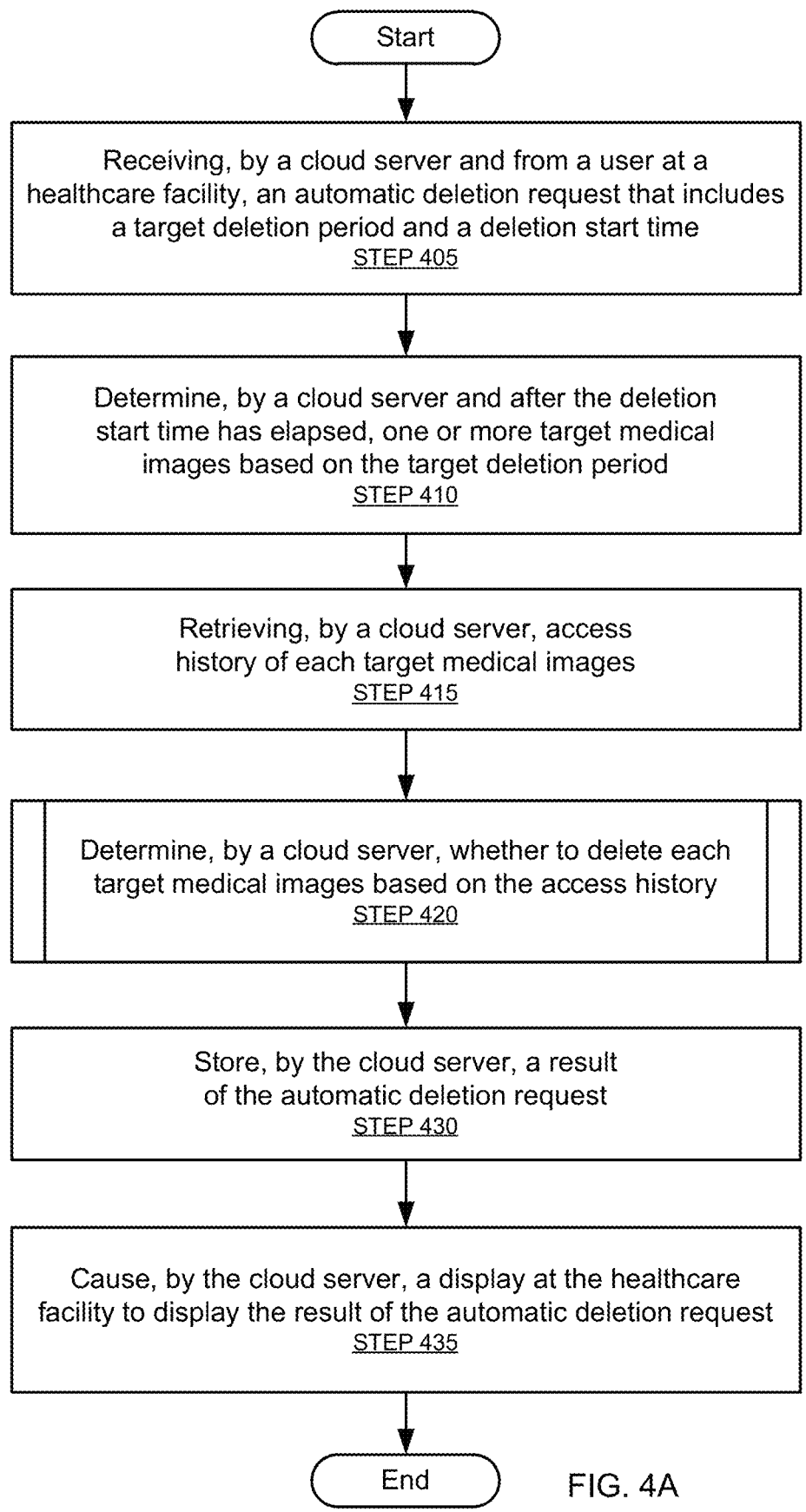
FIG. 4A shows a main flowchart in accordance with one or more embodiments of the invention.
Figure 4B:
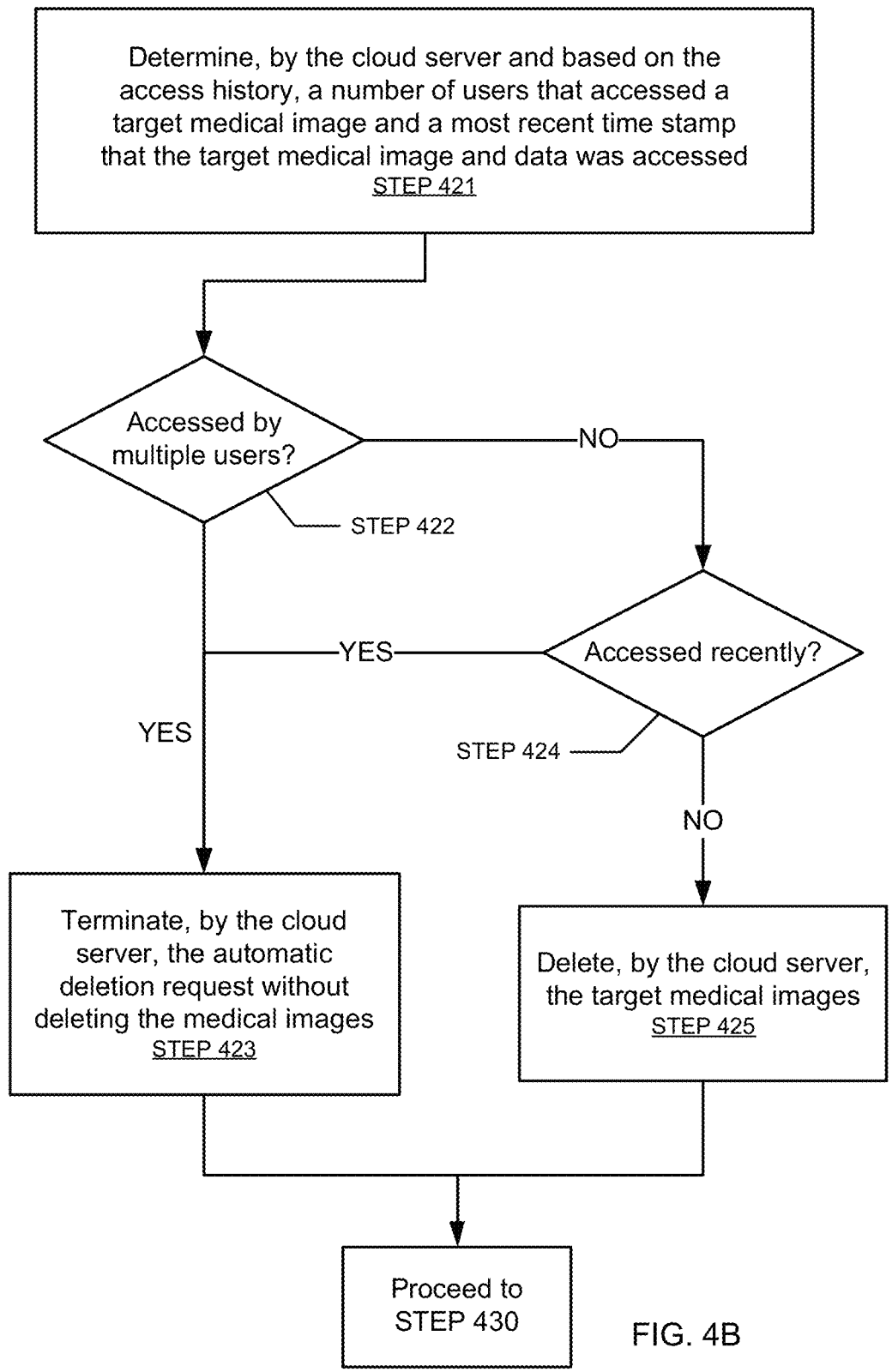
FIG. 4B shows a sub-flowchart in accordance with one or more embodiments of the invention.

FIGS. 4A and 4B show flowcharts in accordance with one or more embodiments of the invention. The flowcharts depict a process for automatically deleting medical images in the cloud server based on access history of the medical images. One or more of the steps in FIGS. 4A and 4B may be performed by the components of the system (100), discussed above in reference to FIGS. 1A-1B and 2B. In one or more embodiments of the invention, one or more of the steps shown in FIGS. 4A and 4B may be omitted, repeated, and/or performed in a different order than the order shown in FIGS. 4A and 4B. Accordingly, the scope of the invention should not be considered limited to the specific arrangement of steps shown in FIGS. 4A and 4B.

Referring to FIG. 4A, initially, in STEP 405, as discussed above in reference to FIGS. 1A-1B and 2B, the cloud server receives an automatic deletion request that includes a target deletion period information and a deletion start time from a user at one of the healthcare facilities connected to the cloud server.

In STEP 410, as discussed above in reference to FIGS. 1A-1B and 2B, after the deletion start time has elapsed, the cloud server determines one or more target medical images based on the target deletion period information.

In STEP 415, as discussed above in reference to FIGS. 1A-1B and 2B, the cloud server retrieves from an internal database (DB) (e.g., a memory) access history of the target medical images.

In STEP 420, as discussed above in reference to FIGS. 1A-1B and 2B, the cloud server determines whether to delete each target medical images based on the access history.

In STEP 430, as discussed above in reference to FIGS. 1A-1B and 2B, the cloud server stores the result of the automatic deletion request in the DB.

In STEP 435, as discussed above in reference to FIGS. 1A-1B and 2B, the cloud server causes a local computing device at the healthcare facility where the automatic deletion request originated to display the result of the automatic deletion request.

FIG. 4B shows a sub-flowchart in accordance with one or more embodiments further expanding upon STEP 420 of the flow chart of FIG. 4A. The sub-flowchart in FIG. 4B depicts, at least in part, the deletion determination based on the access history of the target medical images.

In STEP 421, as discussed above in reference to FIGS. 1A-1B and 2B, the cloud server determines a number of users that have accessed a target medical image and a most recent time stamp that the target medical image was accessed.

In STEP 422, as discussed above in reference to FIGS. 1A-1B and 2B, the cloud server determines whether the target medical image has been accessed by multiple users.

In STEP 423, as discussed above in reference to FIGS. 1A-1B and 2B, the cloud server terminates the automatic deletion request without deleting the target medical image if the target medical image has been accessed by multiple users. In one or more embodiments, if there are multiple target medical images, only the deletion of the target medical images that meet the above criteria will be terminated, the remaining target images and data that do not meet the above criteria will be deleted by the cloud server.

In one or more embodiments of the invention, medical images that have been accessed by multiple users at any of the healthcare facilities may not be deleted. Alternatively, medical images that have been accessed by only users at the same healthcare facility may be deleted In STEP 424, as discussed above in reference to FIGS. 1A-1B and 2B, the cloud server determines if the target medical image has been recently accessed if the target medical image was not previously accessed by multiple users. In one or more embodiments, the time frame that determines whether the target medical image or data was recently accessed may be pre-configured by the vendor(s) of the cloud-based PACS. Alternatively, the time frame may be set through the GUI of the universal viewer client while configuring the automatic deletion request.

If the cloud server determines that the target medical image was not recently accessed, the cloud server deletes the target medical images in STEP 425. If the cloud server determines that the target medical image was recently accessed, the cloud server terminates the automatic deletion request without deleting the target medical image in STEP 423. In one or more embodiments, if there are multiple target images and data, only the deletion of the target images and data that meet the above criteria will be terminated, the remaining target images and data that do not meet the above criteria will be deleted by the cloud server.

In one or more embodiments of the invention, whether the target medical images should be deleted may also be based (in addition or in the alternative) upon the authority level and/or job title of user that previously accessed the target medical images. For example, target medical images that were previously accessed by a radiologist are not to be deleted. In one or more embodiments, the criteria for the authority level and/or type of user associated with medical images that are not to be deleted may be pre-configured by the vendor of the cloud-based PACS. Alternatively, the criteria may be set by the user through the GUI of the universal viewer client while configuring the automatic deletion request.

Figure 5:
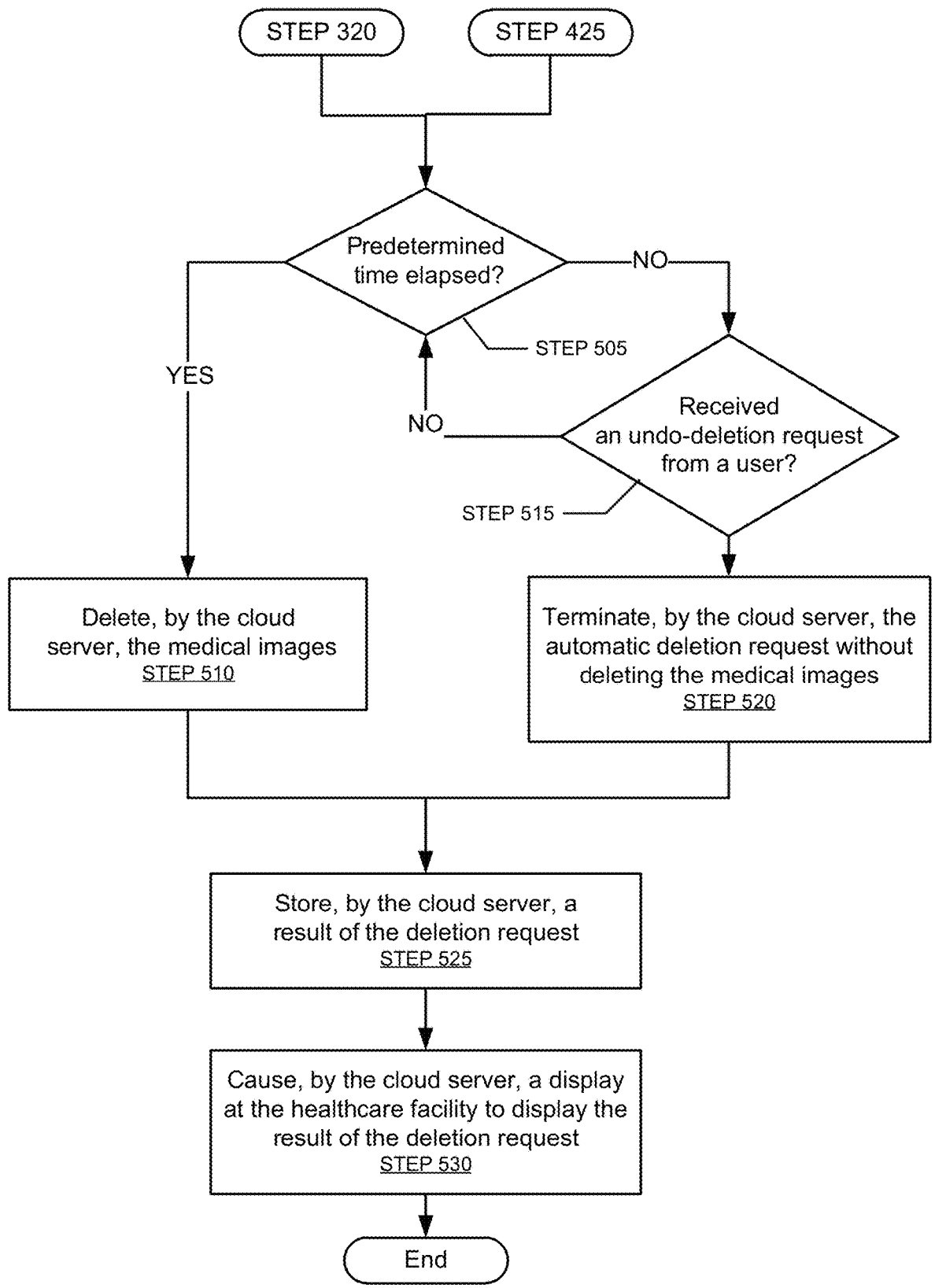
FIG. 5 shows a flowchart in accordance with one or more embodiments.

FIG. 5 shows a flowchart in accordance with one or more embodiments of the invention. The flowcharts depict a process for deleting medical images in the cloud server based on a combination of the deletion according to authority level and the deletion according to access history, as described above in reference to FIGS. 3A-3B and 4A-4B. One or more of the steps in FIG. 5 may be performed by the components of the system (100), discussed above in reference to FIGS. 1A-1B, 2A-2C. In one or more embodiments of the invention, one or more of the steps shown in FIG. 5 may be omitted, repeated, and/or performed in a different order than the order shown in FIG. 5. Accordingly, the scope of the invention should not be considered limited to the specific arrangement of steps shown in FIG. 5.

Initially, in STEP 505, as discussed above in reference to FIGS. 1-4, the cloud server determines whether a predetermined time has elapsed after completion of either or both of STEP 320 and STEP 425. In one or more embodiments, a predetermined time for deletion of the medical image is further included in the automatic deletion request received by the cloud server in STEP 405 of FIG. 4A. In one or more embodiments, the predetermined time for deletion of the automatic deletion request and the predetermined time for deletion of the deletion request (i.e., the deletion request based on authority level) may be different. Alternatively, in some instances, the predetermined time for deletion of the two requests may be the same.

In STEP 510, as discussed above in reference to FIGS. 1-4, the cloud server deletes the medical images if the predetermined time has elapsed.

In STEP 515, as discussed above in reference to FIGS. 1-3, before the predetermined time has elapsed, the cloud server determines whether an undo-deletion request has been received from any user at any of the healthcare facilities. If an undo-deletion was not received, the process reverts to STEP 505 where cloud server continues to determine whether the predetermined time has elapsed. If an undo-deletion was received, the process proceeds to STEP 520 where the cloud server terminates the deletion request without deleting the medical images.

In STEP 525, as discussed above in reference to FIGS. 1-4 the cloud server stores the result of the deletion request in the database (DB).

In STEP 530, as discussed above in reference to FIGS. 1-4, the cloud server causes a local computing device at the healthcare facility where the request originated to display the result of the deletion request.

Figure 6A:
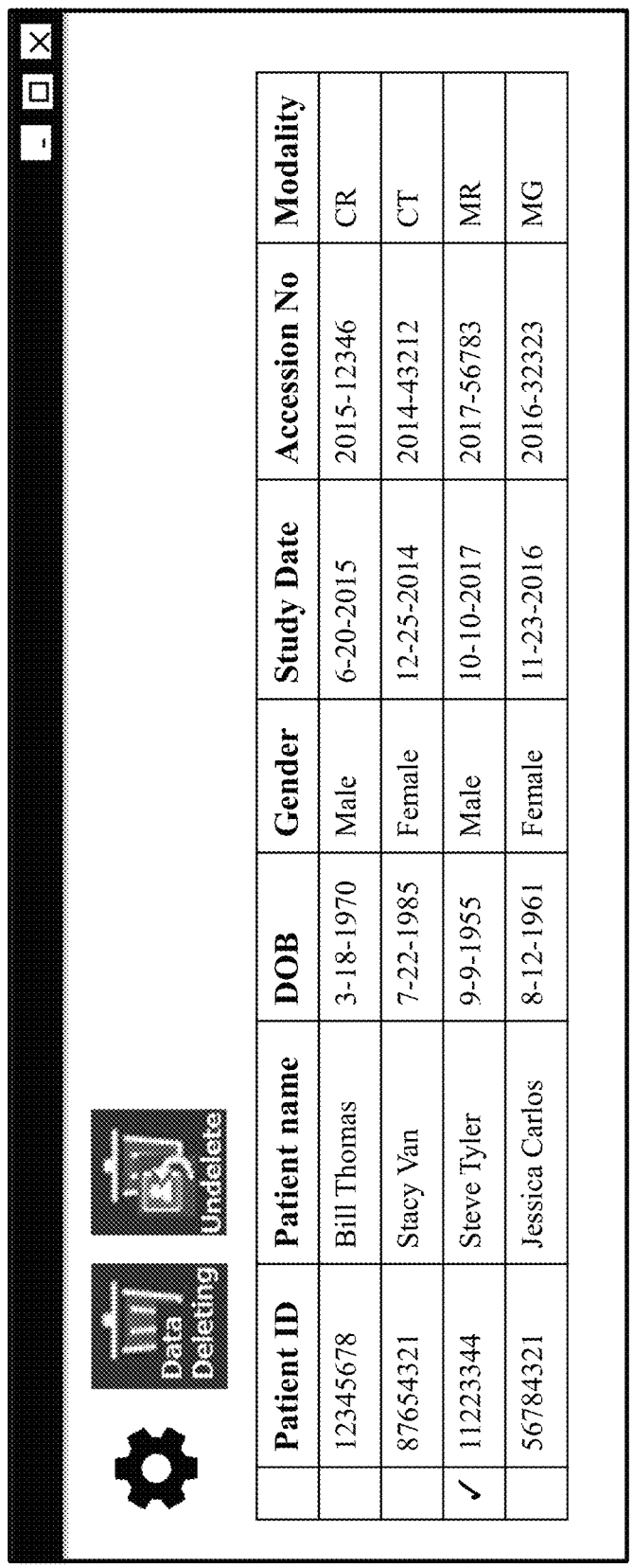
FIG. 6A-6C show an implementation example in accordance with one or more embodiments.
Figure 6B:
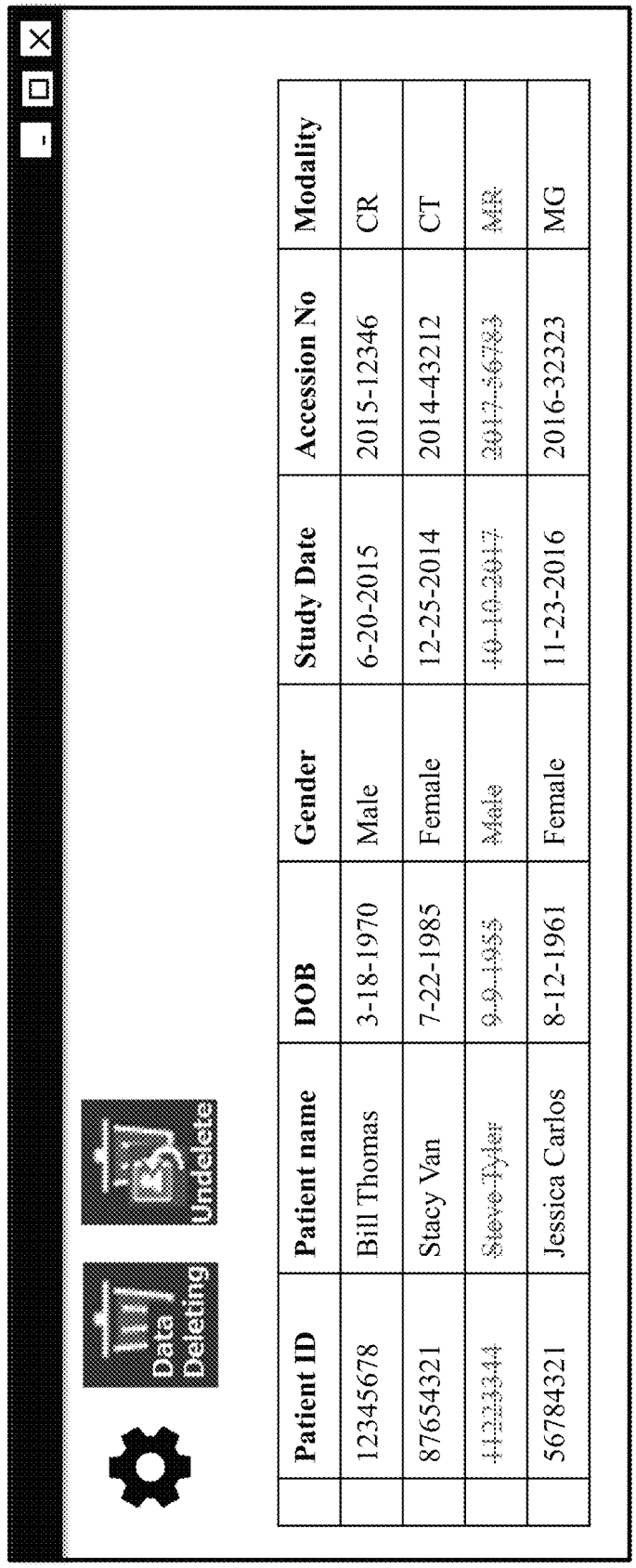
Figure 6C:
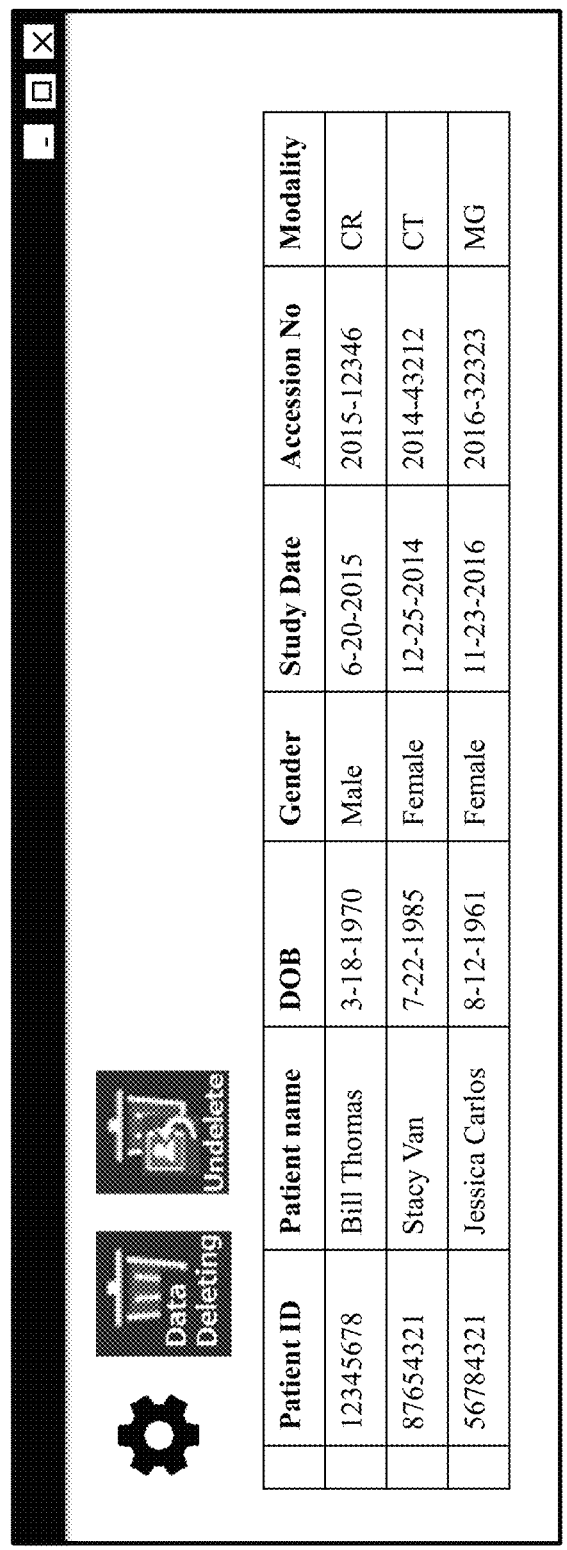

FIGS. 6A-6C show an implementation example in accordance with one or more embodiments of the invention.

FIG. 6A shows a graphical user interface (GUI) displayed in the universal viewer client application that allows a user to select and delete medical images. As seen in FIG. 6A, the medical images are presented in a list form. Each medical image in the list may be presented with a list of information such as patient ID, patient name, patient date of birth (DOB), patient gender, study date of the medical image, accession number of the medical image, and the modality used to perform the diagnosis. Upon selection of a medical image, the user may decide whether to delete the selected data. As further seen in FIG. 6, the medical image for patient Steve Tyler has been selected.

FIG. 6B shows the GUI of FIG. 6A after the user has chosen to delete the medical image for patient Steve Tyler. As seen in FIG. 6B, the deleted medical image for patient Steve Tyler has been struck-through and greyed-out on the list. This is an example of the non-permanent deletion (i.e., temporary deletion) where the actual medical image has not been permanently deleted from the database (DB) of the cloud server. In this state, any user at any of the healthcare facilities may still be able to select and undo the deletion of the medical image for patient Steve Tyler.

FIG. 6C shows the GUI of FIG. 6A after a permanent deletion of a medical image has occurred. As seen in FIG. 6C, the medical image for patient Steve Tyler has been removed from the list of medical images. This indicates that all files associated with the medical images for patient Steve Tyler have been permanently deleted from the DB of the cloud server.

FIG. 7 shows an implementation example in accordance with one or more embodiments of the invention. Specifically, FIG. 7 shows an example graphical user interface (GUI) displayed in the universal viewer client application for a user to set up an automatic deletion request. As seen in FIG. 7, the "Deletion Based On," "Data Type," and "Setting Period" settings make up the target deletion period information that is included in the automatic deletion request. Furthermore, the "Deletion Start Time" setting determines the deletion start time parameter included in the automatic deletion request.

As seen in FIG. 7, the user is able to select exceptions to be considered during the automatic deletion request. The medical images that fit the criteria of the target deletion period will not be deleted if the medical images also fit the criteria in the selected exceptions.

The GUI for configuring the automatic deletion request is not limited to that shown in the example of FIG. 7. In one or more embodiments, additional settings for the automatic deletion request may be added and the existing settings shown in the example of FIG. 7 may be modified to be presented to the user in a different manner.

Figure 8:
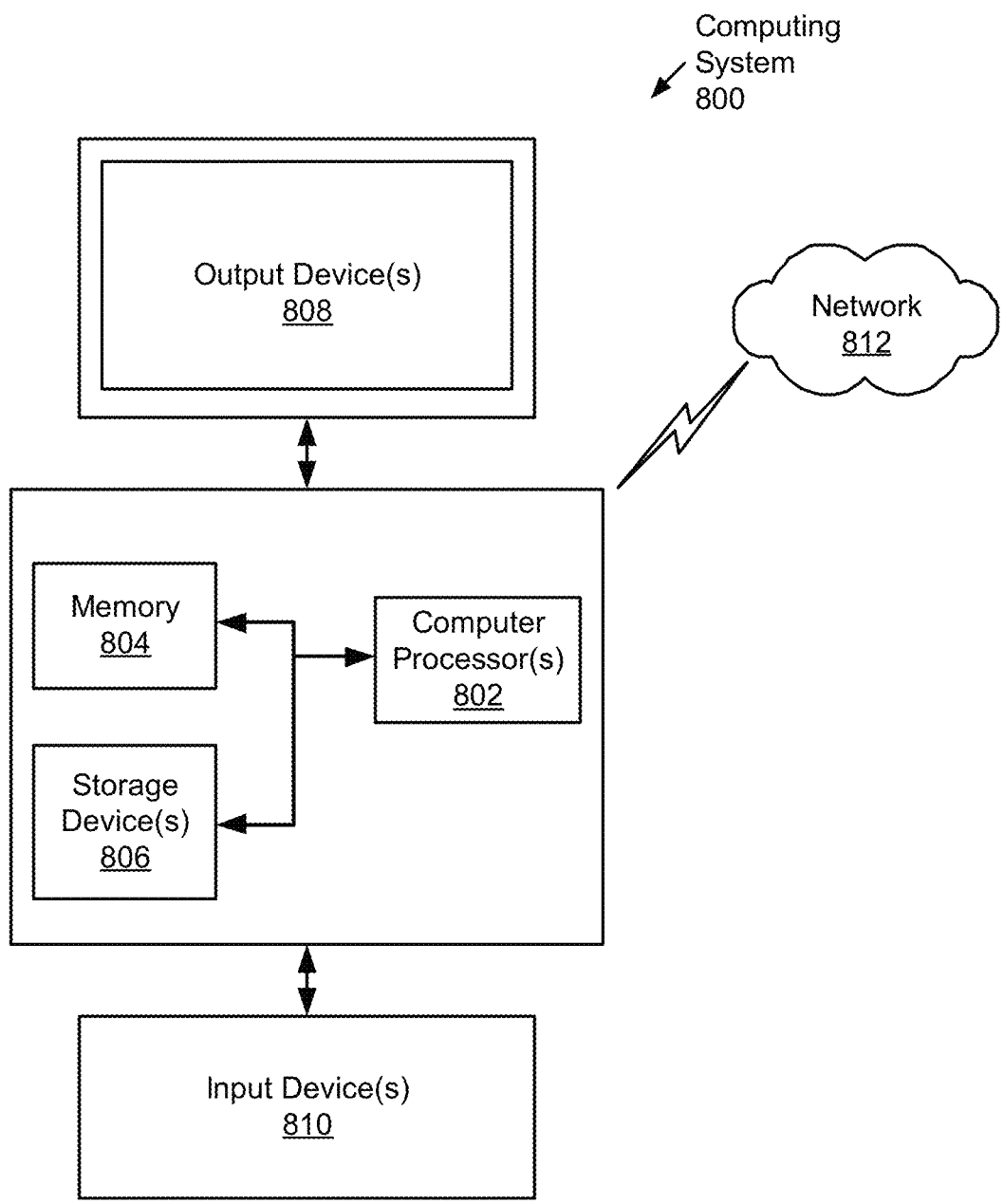
FIG. 8 shows a computing system in accordance with one or more embodiments.

Embodiments of the invention may be implemented on virtually any type of computing system, regardless of the platform being used. For example, the computing system may be one or more mobile devices (e.g., laptop computer, smart phone, personal digital assistant, tablet computer, or other mobile device), desktop computers, servers, blades in a server chassis, or any other type of computing device or devices that includes at least the minimum processing power, memory, and input and output device(s) to perform one or more embodiments of the invention. For example, as shown in FIG. 8, the computing system (800) may include one or more computer processor(s) (802), associated memory (804) (e.g., random access memory (RAM), cache memory, flash memory, etc.), one or more storage device(s) (806) (e.g., a hard disk, an optical drive such as a compact disk (CD) drive or digital versatile disk (DVD) drive, a flash memory stick, etc.), and numerous other elements and functionalities. The computer processor(s) (802) may be an integrated circuit for processing instructions. For example, the computer processor(s) may be one or more cores, or micro-cores of a processor. The computing system (800) may also include one or more input device(s) (810), such as a touchscreen, keyboard, mouse, microphone, touchpad, electronic pen, or any other type of input device. Further, the computing system (800) may include one or more output device(s) (808), such as a screen (e.g., a liquid crystal display (LCD), a plasma display, touchscreen, cathode ray tube (CRT) monitor, projector, or other display device), a printer, external storage, or any other output device. One or more of the output device(s) may be the same or different from the input device(s). The computing system (800) may be connected to a network (812) (e.g., a local area network (LAN), a wide area network (WAN) such as the Internet, mobile network, or any other type of network) via a network interface connection (not shown). The input and output device(s) may be locally or remotely (e.g., via the network (812)) connected to the computer processor(s) (802), memory (804), and storage device(s) (806). Many different types of computing systems exist, and the aforementioned input and output device(s) may take other forms.

Software instructions in the form of computer readable program code to perform embodiments of the invention may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that when executed by a processor(s), is configured to perform embodiments of the invention.

Further, one or more elements of the aforementioned computing system (800) may be located at a remote location and connected to the other elements over a network (812). Further, one or more embodiments of the invention may be implemented on a distributed system having a plurality of nodes, where each portion of the invention may be located on a different node within the distributed system. In one embodiment of the invention, the node corresponds to a distinct computing device. Alternatively, the node may correspond to a computer processor with associated physical memory. The node may alternatively correspond to a computer processor or micro-core of a computer processor with shared memory and/or resources.

The computing system of FIG. 8 may include functionality to present raw and/or processed data, such as results of comparisons and other processing. For example, presenting data may be accomplished through various presenting methods. Specifically, data may be presented through a user interface provided by a computing device. The user interface may include a GUI that displays information on a display device, such as a computer monitor or a touchscreen on a handheld computer device. The GUI may include various GUI widgets that organize what data is shown as well as how data is presented to a user. Furthermore, the GUI may present data directly to the user, e.g., data presented as actual data values through text, or rendered by the computing device into a visual representation of the data, such as through visualizing a data model.

For example, a GUI may first obtain a notification from a software application requesting that a particular data object be presented within the GUI. Next, the GUI may determine a data object type associated with the particular data object, e.g., by obtaining data from a data attribute within the data object that identifies the data object type. Then, the GUI may determine any rules designated for displaying that data object type, e.g., rules specified by a software framework for a data object class or according to any local parameters defined by the GUI for presenting that data object type. Finally, the GUI may obtain data values from the particular data object and render a visual representation of the data values within a display device according to the designated rules for that data object type.

One or more embodiments of the invention may have one or more of the following advantages: the ability to retrieve medical data from all healthcare facilities that are part of a network even though each healthcare facility may implement a different medical data storage system and utilize a different type of network; the ability to prevent deletion of necessary medical images without needing to manually confirm the deletion of each medical image; the ability to conserve memory space in a cloud-based system by automatically deleting unnecessary medical images while automatically preventing the deletion of necessary medical images; the ability to effectively and accurately delete shared medical images in a cloud-based system without the need to manually confirm if the right medical images are deleted during each deletion. These advantages all help save valuable human resources at each healthcare facility.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for controlling automatic deletion of medical images in a universal viewer system that shares the medical images between a cloud server and a plurality of healthcare facilities connected to the cloud server, the method comprising:
   receiving, by the cloud server and from a user at one of the healthcare facilities, an automatic deletion request that comprises a target deletion period and a deletion start time;
   determining, by the cloud server and after the deletion start time has elapsed, a target medical image based on the target deletion period;
   retrieving, by the cloud server, authority information of the user;
   retrieving, by the cloud server, an access history of the target medical image;
   determining, by the cloud server, whether the target medical image is accessed by a plurality of users based on the access history;
   determining, by the cloud server and in response to determining that the target medical image is accessed by a plurality of users, whether the authority information is lower than, matches, or higher than a pre-configured specified authority level;
   upon determining that the authority information is lower than the pre-configured specified authority level, further determining, by the cloud server, that the target medical image should not be deleted and terminating the automatic deletion request without deleting the target medical image, or upon determining that the authority information matches or is higher than a pre-configured specified authority level, further determining, by the cloud server, that the target medical image can be deleted;
   storing in a memory, by the cloud server, a result of the automatic deletion request; and
   causing, by the cloud server, the result of the automatic deletion request to be displayed on a display of at least one of the healthcare facilities.

2. The method according to claim 1, wherein
the plurality of users are located at any of the healthcare facilities including a same healthcare facility as the user, and
the method further comprising:
   deleting, by the cloud sever in response to determining based on the access history that the plurality of users are users at a same healthcare facility, the target medical image.

3. The method according to claim 1, wherein
the access history is stored in a database of the cloud server, and
only a portion of data associated with the target medical image is deleted.

4. The method according to claim 1, wherein:
metadata of the target medical image comprises:
   a receipt date of the target medical image, and
   a study date of the target medical image, and
the receipt date or the study date overlaps with the target deletion period.

5. The method according to claim 1, further comprising:
deleting, by the cloud server in response to determining based on the access history that the target medical image associated with the automatic deletion request is accessed by only a single user, the target medical image associated with the automatic deletion request;
storing in a memory, by the cloud server, the result of the automatic deletion request; and
causing, by the cloud server, the result of the automatic deletion request to be displayed on the display.

6. The method according to claim 5, wherein the single user is the user that sent the automatic deletion request.

7. The method according to claim 1, further comprising:
deleting, by the cloud server in response to determining based on the access history that the target medical image associated with the automatic deletion request is accessed by a plurality of users before an access time, the target medical image associated with the automatic deletion request;
storing in a memory, by the cloud server, the result of the automatic deletion request; and causing, by the cloud server, the result of the automatic deletion request to be displayed on the display.

8. The method according to claim 1, further comprising:
terminating, by the cloud server in response to determining based on the access history that the target medical image associated with the automatic deletion request is accessed by a plurality of users after an access time, the automatic deletion request without deleting the target medical image;
storing, by the cloud server and in a memory, the result of the automatic deletion request; and
causing, by the cloud server, the result of the automatic deletion request to be displayed on the display of at least one of the healthcare facilities.

9. The method according to claim 7, wherein the access time indicates how recently the target medical image associated with the automatic deletion request has been accessed by the users.

10. A non-transitory computer-readable medium (CRM) storing instructions that causes a cloud server to perform an operation for controlling automatic deletion of medical images in a universal viewer system that shares the medical images between the cloud server and a plurality of healthcare facilities connected to the cloud server, the operation comprising causing the cloud server to:
receive, from a user at one of the healthcare facilities, an automatic deletion request that comprises a target deletion period and a deletion start time;
determine, after the deletion start time has elapsed, a target medical image based on the target deletion period;
retrieve authority information of the user;
retrieve an access history of the target medical image;
determine whether the target medical image is accessed by a plurality of users based on the access history;
determine, in response to determining that the target medical image is accessed by a plurality of users, whether the authority information is lower than, matches, or higher than a pre-configured specified authority level;
upon determining that the authority information is lower than the pre-configured specified authority level, further determine that the target medical image should not be deleted and terminate the automatic deletion request without deleting the target medical image, or upon determining that the authority information matches or is higher than a pre-configured specified authority level, further determine that the target medical image can be deleted;
store, in a memory, a result of the automatic deletion request; and
cause the result of the automatic deletion request to be displayed on a display of at least one of the healthcare facilities.

11. The non-transitory CRM according to claim 10, wherein
the plurality of users are located at any of the healthcare facilities including a same healthcare facility as the user, and
the method further comprising:
deleting, by the cloud sever in response to determining based on the access history that the plurality of users are users at a same healthcare facility, the target medical image.

12. The non-transitory CRM according to claim 10, wherein the access history is stored in a database of the cloud server, and
only a portion of data associated with the target medical image is deleted.

13. The non-transitory CRM according to claim 10, wherein:
metadata of the target medical image comprises:
a receipt date of the target medical image, and
a study date of the target medical image, and
the receipt date or the study date overlaps with the target deletion period.

14. The non-transitory CRM according to claim 10, the operation further comprising causing the cloud server to:
delete, in response to determining based on the access history that the target medical image associated with the automatic deletion request is accessed by only a single user, the target medical image associated with the automatic deletion request;
store, in a memory, the result of the automatic deletion request; and
cause the result of the automatic deletion request to be displayed on the display.

15. The non-transitory CRM according to claim 14, wherein the single user is the user that sent the automatic deletion request.

16. A universal viewer system that controls deletion of medical images, the universal viewer system comprising:
a cloud server; and
a plurality of local computers disposed at healthcare facilities connected to the cloud server, wherein
the universal viewer system shares the medical images between the cloud server and the local computers, and
the cloud server:
receives, from a user at one of the healthcare facilities, an automatic deletion request that comprises a target deletion period and a deletion start time;
determines, after the deletion start time has elapsed, a target medical image based on the target deletion period;
retrieves authority information of the user;
retrieves an access history of the target medical image;
determines whether the target medical image is accessed by a plurality of users based on the access history;
determines, in response to determining that the target medical image is accessed by a plurality of users, whether the authority information is lower than, matches, or higher than a pre-configured specified authority level;
upon determining that the authority information is lower than the pre-configured specified authority level, further determines that the target medical image should not be deleted and terminates the automatic deletion request without deleting the target medical image, or upon determining that the authority information matches or is higher than a pre-configured specified authority level, further determines that the target medical image can be deleted;
stores, in a memory, a result of the automatic deletion request; and
causes the result of the automatic deletion request to be displayed on a display of at least one of the healthcare facilities.

17. The universal viewer system according to claim 16, wherein the plurality of users are located at any of the healthcare facilities including a same healthcare facility as the user, and the method further comprising:

deleting, by the cloud sever in response to determining based on the access history that the plurality of users are users at a same healthcare facility, the target medical image.

18. The universal viewer system according to claim 16, wherein the access history is stored in a database of the cloud server, and only a portion of data associated with the target medical image is deleted.

19. The universal viewer system according to claim 16, wherein:

metadata of the target medical image comprises:
 a receipt date of the target medical image, and
 a study date of the target medical image, and
the receipt date or the study date overlaps with the target deletion period.

20. The universal system according to claim 16, wherein the cloud server further:

deletes, in response to determining based on the access history that the target medical image associated with the automatic deletion request is accessed by only a single user, the target medical image associated with the automatic deletion request;

stores, in a memory, the result of the automatic deletion request; and causes the result of the automatic deletion request to be displayed on the display, wherein the single user is the user that sent the automatic deletion request.

21. The method according to claim 1, wherein upon determining that the target medical image should be deleted, non-permanently deleting, by the cloud server, the target medical image, and after a predetermined time elapses, permanently deleting data associated with the target medical image, and the predetermined time is based on an authority level of the user.

* * * * *